(12) United States Patent
Abbott

(10) Patent No.: US 9,067,850 B2
(45) Date of Patent: Jun. 30, 2015

(54) SYNTHESIS GAS AND FISCHER TROPSCH INTEGRATED PROCESS

(75) Inventor: Peter Edward James Abbott, Eaglescliffe Cleveland (GB)

(73) Assignee: JOHNSON MATTHEY PUBLIC LIMITED COMPANY, London (GB)

(*) Notice: Subject to any disclaimer, the term of this patent is extended or adjusted under 35 U.S.C. 154(b) by 0 days.

(21) Appl. No.: 14/345,554

(22) PCT Filed: Jul. 23, 2012

(86) PCT No.: PCT/GB2012/051761
§ 371 (c)(1),
(2), (4) Date: Mar. 18, 2014

(87) PCT Pub. No.: WO2013/038140
PCT Pub. Date: Mar. 21, 2013

(65) Prior Publication Data
US 2014/0357737 A1    Dec. 4, 2014

(30) Foreign Application Priority Data

Sep. 15, 2011 (GB) .................................. 1115929.0

(51) Int. Cl.
| | |
|---|---|
| C07C 27/06 | (2006.01) |
| C07C 1/04 | (2006.01) |
| C07C 29/151 | (2006.01) |
| C10K 1/00 | (2006.01) |
| C10K 1/04 | (2006.01) |
| C10K 3/04 | (2006.01) |
| C10G 2/00 | (2006.01) |
| C01B 3/16 | (2006.01) |
| C01B 3/38 | (2006.01) |
| B01D 53/22 | (2006.01) |

(52) U.S. Cl.
CPC ........... *C07C 1/0485* (2013.01); *C07C 29/1518* (2013.01); *C10K 1/005* (2013.01); *C10K 1/04* (2013.01); *C10K 3/04* (2013.01); *C10G 2/30* (2013.01); *B01D 53/229* (2013.01); *C01B 3/16* (2013.01); *C01B 3/38* (2013.01); *C01B 2203/0233* (2013.01); *C01B 2203/0244* (2013.01); *C01B 2203/0255* (2013.01); *C01B 2203/0261* (2013.01); *C01B 2203/0283* (2013.01); *C01B 2203/0405* (2013.01); *C01B 2203/0415* (2013.01); *C01B 2203/043* (2013.01); *C01B 2203/0475* (2013.01); *C01B 2203/0495* (2013.01); *C01B 2203/062* (2013.01)

(58) Field of Classification Search
CPC ........................ C07C 1/0485; C07C 29/1518
USPC ................................................. 518/704, 705
See application file for complete search history.

(56) References Cited

U.S. PATENT DOCUMENTS

| | | | |
|---|---|---|---|
| 2011/0098367 A1* | 4/2011 | Assink et al. .................. | 518/705 |
| 2012/0103190 A1 | 5/2012 | Wallace | |

FOREIGN PATENT DOCUMENTS

| | | |
|---|---|---|
| EP | 0157480 A2 | 10/1985 |
| EP | 1188713 A2 | 3/2002 |
| EP | 1403216 A1 | 3/2004 |
| EP | 1413547 A1 | 4/2004 |
| EP | 1438259 | 7/2004 |
| GB | 2407818 A | 5/2005 |
| WO | 9906138 A1 | 2/1999 |
| WO | 0009441 A2 | 2/2000 |
| WO | 03016250 A1 | 2/2003 |
| WO | 03036166 A2 | 5/2003 |
| WO | 03062142 A1 | 7/2003 |
| WO | 2004041716 A1 | 5/2004 |
| WO | 2006037782 A1 | 4/2006 |
| WO | 2007069197 A2 | 6/2007 |

OTHER PUBLICATIONS

David Edlund, "Hydrogen Membrane Technologies and Application in Fuel Processing" chapter 8; Jin Huang et al., "C02-Selective Membranes for Hydrogen Fuel Processing", chapter 9; In: Hydrogen and Syngas Production and Purification Technologies, Dec. 31, 2010, XP002684726.
Gandrik et al., "HTGR-Integrated Coal to Liquids Production Analysis", Idaho National Laboratory, 2010 International Pittsburgh Coal Conference, 2010, pp. 1-16, XP002684724.
Kreutz et al., "Fischer-Tropsch Fuels from Coal and Biomass", 25th Annual International Pittsburgh Coal Conference, 2008, Princeton Environmental Institute, XP002684725.
Spyrakis et al., "Synthesis, Modeling and Exergy Analysis of Atmospheric Air Blown Biomass Gasification for Fischer-Tropsch Process", Int. Centre for Applied Thermodynamics (ICAT), 2009, vol. 12, No. 4, pp. 187-192, XP002684723.
GB Search Report, dated Oct. 10, 2012, from corresponding GB application.
International Search Report, dated Oct. 8, 2012, from corresponding PCT application.
GB Search Report, dated Jan. 12, 2012, from corresponding GB application.

\* cited by examiner

*Primary Examiner* — Sudhakar Katakam
(74) *Attorney, Agent, or Firm* — Young & Thompson

(57) ABSTRACT

Process for synthesizing hydrocarbons includes: reforming a hydrocarbon feedstock containing inert gases in reforming stages to generate a synthesis gas including the inert gases, steam, hydrogen and carbon monoxide; cooling the synthesis gas below the dew point to obtain a dewatered synthesis gas; synthesizing hydrocarbons from the dewatered synthesis gas by the Fischer-Tropsch reaction and separating at least part of the synthesized hydrocarbons, to give a tail gas; subjecting a mixture of at least part of the tail gas and steam to the water-gas shift reaction, to form shifted tail gas having increased hydrogen and carbon dioxide contents; subjecting the shifted tail gas to one or more membrane separation stages thereby generating an inert gas-containing gas mixture and one or more of a hydrogen-, carbon dioxide- and a hydrocarbon-containing gas mixture; and using one or more of the hydrogen-, carbon dioxide- and hydrocarbon-containing gas mixture in a reformer feed stream.

13 Claims, 3 Drawing Sheets

SYNTHESIS GAS AND FISCHER TROPSCH INTEGRATED PROCESS

This invention relates to an improved process for the production of hydrocarbons, and in particular to an improved integrated reforming and Fischer-Tropsch hydrocarbon synthesis process.

Reforming of hydrocarbons such as natural gas to generate synthesis gases comprising hydrogen and carbon oxides suitable for the Fischer-Tropsch (FT) synthesis of liquid hydrocarbons may be accomplished by steam reforming, autothermal reforming or partial oxidation processes.

Integration of the Fischer-Tropsch process with upstream reforming offers a number of advantages.

WO 00/09441 describes a process comprising subjecting a hydrocarbon feedstock/steam mixture to primary steam reforming over a catalyst disposed in heated tubes in a heat exchange reformer, subjecting the resultant primary reformed gas to secondary reforming by partially combusting the primary reformed gas with an oxygen-containing gas and bringing the resultant partially combusted gas towards equilibrium over a secondary reforming catalyst, with the resultant secondary reformed gas used to heat the tubes of the heat exchange reformer. Carbon dioxide is separated from the secondary reformed gas before or after its use for the synthesis of carbon containing compounds, and is recycled to the primary reformer feed. In one embodiment, the recycled carbon dioxide is part of the tail gas from a Fischer-Tropsch synthesis process, and is added to the natural gas feedstock prior to desulphurisation.

WO 03/016250 describes a process in which a synthesis gas for the Fischer-Tropsch process is generated in steps of primary and secondary reforming where a Fischer-Tropsch tail gas is added to a the primary reformed gas before partial combustion thereof, i.e. addition of tail gas to the primary reformed gas between the steps of primary and secondary reforming. Such addition, where carbon dioxide is present in the tail gas or is added from another source, further has the effect of allowing lower steam ratios to be used in the primary reformer. This has advantages in respect of providing lower operating costs, for example in steam generation.

WO04/041716 describes a process in which a synthesis gas for the Fischer-Tropsch process is generated in steps of primary and secondary reforming with Fischer-Tropsch tail gas added to the primary reformed gas, wherein the hydrocarbon feed is divided and fed to both the primary and secondary reformers.

However efficient recycle of the Fisher-Tropsch tail gas to the reforming processes is limited by the presence of inert gases, particularly nitrogen, present in the hydrocarbon feedstock. High nitrogen levels dilute the content of reactants and increase the size of equipment throughout the process. We have devised a process that overcomes the problems caused by the presence of such inert gases.

Accordingly, the invention provides a process for the synthesis of hydrocarbons comprising the steps of; (i) reforming a hydrocarbon feedstock containing one or more inert gases in one or more reforming stages to generate a synthesis gas comprising the one or more inert gases, steam, hydrogen and carbon monoxide, (ii) cooling the synthesis gas to below the dew point to condense water and removing the water to give a de-watered synthesis gas, (iii) synthesising hydrocarbons from said de-watered synthesis gas by the Fischer-Tropsch reaction and separating at least part of the synthesised hydrocarbons, to give a tail gas comprising the one or more inert gases, hydrogen, carbon monoxide and carbon dioxide, (iv) subjecting a mixture of at least part of the tail gas and steam to the water-gas shift reaction, thereby forming a shifted tail gas having increased hydrogen and carbon dioxide contents, (v) subjecting the shifted tail gas to one or more stages of membrane separation thereby generating an inert gas-containing gas mixture and one or more of a hydrogen-containing gas mixture, a carbon dioxide-containing gas mixture and a hydrocarbon-containing gas mixture, and (vi) using one or more of said hydrogen-containing gas mixture, said carbon dioxide-containing gas mixture and said hydrocarbon-containing gas mixture in a reformer feed stream.

The hydrocarbon feedstock may be any gaseous or low boiling hydrocarbon feedstock such as natural gas or naphtha. The hydrocarbon feedstock is preferably natural gas, including associated gas, more preferably a natural gas containing over 90% vol methane, but an advantage of the present invention is that less pure hydrocarbon feedstocks may be used. The one or more inert gases may comprise principally nitrogen. Argon may also be present. The nitrogen content of the hydrocarbon feedstock may be in the range 0.1-15% by volume. The nitrogen content of the hydrocarbon feedstock is preferably ≤10% vol, more preferably 5% vol. The feedstock is typically compressed to a pressure in the range 20-60 bar abs.

If the feedstock contains sulphur compounds, before, or preferably after compression, the feedstock is desirably subjected to desulphurisation, comprising hydrodesulphurisation in the presence of hydrogen over a hydrodesulphurisation catalyst such as a supported Co and/or Ni and Mo and/or W catalyst with subsequent absorption of hydrogen sulphide using a suitable absorbent, such as a zinc oxide-containing composition.

The synthesis gas mixture may be provided by a number of methods. Preferably the reforming step includes a step of steam reforming and/or a step of partial oxidation and/or a step of autothermal reforming. The reforming step may also include a step of pre-reforming.

Preferably the reforming step includes a step of partial oxidation, including catalytic or non-catalytic partial oxidation, autothermal or secondary reforming.

In pre-reforming, the hydrocarbon feedstock/steam mixture is heated, typically to a temperature in the range 350-650° C., and then passed adiabatically through a bed of a suitable catalyst, usually a nickel catalyst having a high nickel content, for example above 40% by weight.

In contrast, primary steam reforming is usually effected at outlet temperatures above about 600° C., typically in the range 650° C. to 950° C., by passing the feedstock/steam mixture over a primary steam reforming catalyst disposed in externally heated tubes arranged in a heat exchange reformer. The heat exchange reformer inlet temperature is typically in the range 300-500° C. The amount of steam preferably used is such as to give a steam ratio of 0.5 to 2, i.e. 0.5 to 2 moles of steam per gram atom of hydrocarbon carbon in the feedstock. The amount of steam is preferably minimised as this leads to a lower cost, more efficient process. It is preferred that the steam ratio is below 1.5, more preferably 0.5 to 1.0. The primary reforming catalyst may be nickel supported on a refractory support such as rings or pellets of calcium aluminate cement, alumina, titania, zirconia and the like. Alternatively, particularly when a steam ratio less than 1.0 is employed, a precious metal catalyst may be used as the primary reforming catalyst. Suitable precious metal catalysts include rhodium, ruthenium and platinum between 0.01 and 2% by weight on a suitable refractory support such as those used for nickel catalysts. Alternatively a combination of a nickel and precious metal catalyst may be used. The composition of the product gas depends on, inter alia, the proportions of the feedstock components, the pressure and temperature. For applications such as Fischer-Tropsch synthesis, it is desired that the molar ratio of hydrogen to carbon monoxide is about 2 and the amount of carbon dioxide present is small.

In order to obtain a synthesis gas better suited to a Fischer-Tropsch process, the pre-reformed or primary reformed gas may be subjected in an autothermal or secondary reformer to further reforming reactions comprising (i) partial combustion of the reformed gas with a suitable oxidant, e.g. air, oxygen or oxygen-enriched air which may also contain some steam, using burner apparatus mounted near the top of the reformer and (ii) adiabatic catalytic steam reforming of the partially combusted gas over a bed of a steam reforming catalyst, such as nickel on alumina pellets disposed below the burner apparatus, to bring the gas composition towards equilibrium. The partial combustion reactions are exothermic and the temperature of the partially combusted reformed gas is increased to between 1000 and 1500° C. Thus the energy for the endothermic steam reforming reaction is supplied by the hot, partially combusted reformed gas. As the partially combusted reformed gas contacts the steam reforming catalyst it is cooled by the steam reforming reaction to an exit temperature in the range 800-1100° C. In a preferred arrangement, especially where the oxidant is oxygen, the steam reforming catalyst comprises a first layer comprising a catalytically-active metal on a zirconia support, especially rhodium on a zirconia support, followed by a second layer comprising nickel on a refractory support such as alumina. Such catalyst beds are described in WO2006/126018, herein incorporated by reference.

Alternatively, the feed to the partial combustion step may be a desulphurised hydrocarbon feedstock/steam mixture, or a mixture of reformed gas and desulphurised hydrocarbon feedstock and optionally steam.

Reforming by partial oxidation, rather than autothermal or secondary reforming, may be effected on the desulphurised hydrocarbon or a pre-reformed gas mixture using an oxygen-containing gas. Partial oxidation may be catalytic (CPO) or non-catalytic (POx). Suitable catalysts are supported precious metals, such as platinum, palladium, rhodium, ruthenium, rhenium and iridium.

Other suitable reforming processes include combining primary reforming, or primary and secondary reforming, with parallel autothermal reforming. Such processes are described in EP1403216 and EP1413547.

Additionally or alternatively, the reforming may include one or more steps of partial oxidation alone or preferably in combination with steam reforming or autothermal reforming. Suitable processes are described in WO 2006/037782, EP 1438259 and EP 1188713.

If desired, the hydrocarbon feedstock may be divided into two or more streams, which may be fed in parallel to the different reforming stages. For example, the hydrocarbon feedstock may be divided into two streams, the first stream mixed with steam and subjected to a step of steam reforming and the second stream fed, optionally following a step of pre-reforming, to a partial oxidation reactor or to a secondary or autothermal reformer. In one embodiment, utilising a gas-heated reformer in combination with a secondary reformer, the hydrocarbon feedstock is divided into first and second streams and added separately to the reforming stages of the synthesis gas generation process. In this case, the second hydrocarbon stream may comprise between 5 and 50% by volume, preferably between 5 and 40% by volume and most preferably between 5 and 30% by volume of the hydrocarbon feedstock.

In the present invention, by providing a proportion of the hydrocarbon feedstock and at least part of one or more of the hydrogen-containing gas, carbon dioxide-containing gas or hydrocarbon-containing gas mixture separated from the Fischer-Tropsch tail gas to a reformer feed stream, it is possible to operate the process at low overall steam ratios (particularly steam ratios 1.0) with reduced risk of carbon deposition.

In a first preferred embodiment, the reforming step comprises autothermal reforming wherein a hydrocarbon feedstock/steam mixture, or pre-reformed gas mixture containing hydrocarbon, hydrogen, steam and carbon oxides, is fed to an autothermal reformer where it is partially combusted with an oxygen-containing gas and the partially combusted gas passed through a bed of steam reforming catalyst to create the synthesis gas. In a second preferred embodiment, the reforming step comprises subjecting the desulphurised hydrocarbon feedstock/steam mixture to a step of partial oxidation or catalytic partial oxidation with an oxygen-containing gas.

In these embodiments, the feed stream for the partial oxidation or autothermal reforming process, which may be a pre-reformed or steam reformed gas mixture, additionally comprises a portion of one or more of the hydrogen-containing gas, the carbon dioxide-containing gas and the hydrocarbon-containing gas separated from the shifted Fischer-Tropsch tail gas and, where parallel reforming of the hydrocarbon feedstock is employed, a hydrocarbon stream. In forming the feed stream, the hydrogen-containing gas, the carbon dioxide-containing gas and the hydrocarbon-containing gas separated from the shifted Fischer-Tropsch tail gas and/or hydrocarbon stream, may be combined with the reformed gas in any order. However, if a tail gas component and hydrocarbon are combined with the reformed feed gas, pre-mixing the tail gas component and second hydrocarbon stream has the advantage that, if necessary, they may be heated together in one rather than two heat exchangers.

The product synthesis gas typically contains hydrogen, carbon dioxide, carbon monoxide, steam, residual unreacted hydrocarbon such as methane and any gas, such as nitrogen, that is present in the feed and which is inert under the conditions employed.

Howsoever the synthesis gas is generated, it is necessary before it is used for the Fischer-Tropsch synthesis of hydrocarbons, to remove the water. In order to remove water from the synthesis gas, the synthesis gas is cooled to below the dew point at which water condenses. Such cooling may be effected using a stream of cold water and/or by indirect heat exchange using methods known in the art. The water condensate is separated from the synthesis gas using for example, a separator. Heat recovered during this cooling may be employed for pre-heating duties and may be used to boil water, e.g. the process condensate and/or preferably the Fischer-Tropsch co-produced water, used to provide the steam for a steam reforming stage.

Typically a de-watered synthesis gas may contain 5 to 15% by volume of carbon dioxide. In one embodiment of the invention, after separation of the condensed water, carbon dioxide is separated from the de-watered synthesis gas prior to the Fischer-Tropsch synthesis stage and recycled to the reforming stage. The recycled carbon dioxide stream may be added to the hydrocarbon feed gas but is preferably added to a partial combustion stage feed stream. Where the recycled carbon dioxide (either as carbon dioxide separated from the synthesis gas prior to synthesis and recycled, or as a component separated from the recycled shifted Fischer-Tropsch tail gas) is added to the partial combustion stage feed stream, rather than to the hydrocarbon feed gas, there is an advantage in that the steam reforming process can be operated at a lower steam ratio.

The carbon dioxide may be separated from the de-watered synthesis gas by a conventional "wet" process or alternatively a pressure swing adsorption process may be employed. In a conventional "wet" process the crude synthesis gas is de-watered and is then contacted with a stream of a suitable absorbent liquid, such as an amine, particularly methyl diethanolamine (MDEA) solution so that the carbon dioxide is absorbed by the liquid to give a laden absorbent liquid and a gas stream having a decreased content of carbon dioxide. The laden absorbent liquid is then regenerated, for example by heating, to desorb the carbon dioxide and to give a regenerated absorbent liquid, which is then recycled to the carbon dioxide absorption stage.

Alternatively, or in addition to a stage of carbon dioxide separation and recycle, before the de-watered synthesis gas is passed to the Fischer-Tropsch hydrocarbon synthesis stage it may, if desired, be further subjected to a step of hydrogen separation, e.g. through a membrane, in order to provide pure hydrogen for other uses e.g. hydrocracking of product Fischer-Tropsch liquids or hydrodesulphurisation of the hydrocarbon feedstock. However, the hydrogen for this purpose may instead be recovered from the shifted Fischer-Tropsch tail gas.

The de-watered synthesis gas will contain the one or more inert gases present in the hydrocarbon feedstock. Carbon dioxide separation from the de-watered synthesis gas may be utilised to adjust the stoichiometry of the synthesis gas fed to the Fischer-Tropsch reaction. However it is not necessary in the present invention to employ this step.

In the Fischer-Tropsch process, a synthesis gas containing carbon monoxide and hydrogen is reacted in the presence of a catalyst, which is typically a reduced cobalt- and/or iron-containing composition. Water is a co-product in the reaction, which may be described as follows;

$$nCO + 2nH_2 \rightarrow (CH_2)_n + nH_2O$$

The synthesis gas preferably has a hydrogen:carbon monoxide ratio in the range 1.7-2.5:1. The reaction may be performed in a continuous or batch process using one or more fixed bed, stirred slurry-phase reactors, bubble-column reactors, loop reactors or fluidised bed reactors. The process may be operated at pressures in the range 0.1-10 Mpa and temperatures in the range 150-350° C. The gas-hourly-space velocity (GHSV) for continuous operation is in the range 100-25000 hr$^{-1}$. The synthesised hydrocarbon, preferably having n≥5, and co-produced water are separated from the residual gas. The reaction may be carried out in a single pass or preferably part of the residual gas is combined with fresh synthesis gas and recycled to the Fischer-Tropsch reactor in a loop.

The synthesised hydrocarbon product is separated from the co-produced water. This may be achieved using one or more separators and techniques known to those skilled in the art.

The residual gas from such separation is divided and a portion may be sent back to the Fischer-Tropsch stage as a recycle stream. The portion returned is preferably a major portion (i.e. >50% vol of the residual gas), with a minor portion recovered as the tail gas.

Any residual gas which is not recycled to the Fischer-Tropsch reactor for further reaction is herein termed tail gas. Since the reaction of the synthesis gas is usually incomplete, the tail gas will contain some hydrogen and carbon monoxide as well as the one or more inert gases fed into the process from the hydrocarbon feedstock. In addition, the tail gas may also contain some light hydrocarbons, e.g. paraffins including methane, ethane, propane, butane, olefins such as propylene, alcohols such as ethanol, and traces of other minor components such as organic acids. It will generally also contain some carbon dioxide, which may be present in the synthesis gas fed to the Fischer-Tropsch reaction and/or is formed by side reactions. The tail gas may be further treated (e.g. by means including refrigeration) to remove more light hydrocarbons, e.g. pentane, butane and propane. These components of the tail gas represent a valuable source of carbon and hydrogen.

In the present invention, at least a portion of the tail gas, mixed with steam, is subjected to the water gas shift reaction that increases the hydrogen and carbon dioxide content of the tail gas according to the following reaction:

$$CO + H_2O \leftrightarrow CO_2 + H_2$$

The shift stage is required due to the poor separation of carbon monoxide from inert gases. By forming carbon dioxide, the valuable carbon may be more readily separated from the inert gases and recycled to the process. Another advantage is that the shift catalyst may be active for olefin hydrogenation so that any olefins present in the tail gas may be conveniently converted to paraffins. The water-gas shift reaction, which is exothermic, may be performed adiabatically or preferably pseudo-isothermally in a heat-exchange reactor, using copper-based water gas shift catalysts, especially copper/zinc oxide/alumina water gas shift catalysts. In a pseudo-isothermal water gas shift stage, the coolant conveniently is water under such a pressure such that partial, or complete, boiling takes place. A suitable pressure is 15 to 50 bar abs and the resulting steam can be used, for example, to drive a turbine or to provide process steam for the water-gas shift reaction, or for an upstream stage in which the shift feed gas is generated. The water can be in tubes surrounded by catalyst or vice versa. Two particular modes of operating this type of shift process are envisaged:

(i) Falling temperature profile, for example 240 to 350° C. inlet range and (especially 240 to 310° C.) with typically a fall of up to 50° C. (especially 10 to 30° C.) between inlet and outlet; and (ii) Rising temperature profile, for example at an inlet temperature in the range 100 to 240° C. rising to a maximum of 240 to 350° C., followed by a falling temperature profile as in (i) above. The hot water in heat exchange brings the feed gas up to the temperature at which the shift reaction proceeds rapidly. In such a process, the inlet zone in the shift catalyst bed may be a preheat zone charged with inert granules such as alpha alumina.

In any such shift processes it may be desirable to protect the catalyst from poisoning, such as by sulphur or chlorine compounds, and for this purpose a guard bed of expendable catalyst or zinc oxide or alkalised alumina can be disposed upstream.

Processes involving heat exchange are described further in EP-A-157480. The provision of the heat exchange also assists in controlling catalyst temperature during reductive activation and also, by coping with any fall in temperature below the dew point of steam, makes it practicable to use a chloride guard, such as alkalised alumina, in an inlet zone above the catalyst.

The shifted Fischer-Tropsch tail gas is desirably cooled to below the dew point and condensed water removed, e.g. using one or more separators, before feeding it to the one or more membrane separation steps.

The membrane separation on the shifted Fischer-Tropsch tail gas may be performed in one or more, preferably two or more stages, which may be operated in series or in parallel using conventional membrane technology. In all embodiments it is preferred to use the hydrocarbon feedstock, especially a natural gas, as a component of the sweep gas in the one or more of the membrane separation units. In this way the hydrocarbon feedstock may be enriched with the desired component or components of the shifted Fischer-Tropsch tail gas.

In one embodiment, the shifted Fischer-Tropsch tail gas is fed to a first membrane separation unit fed with a desulphurised natural gas as the sweep gas. The membrane in said first unit is hydrogen-selective and a hydrogen-containing gas mixture is separated as permeate from the shifted Fischer-Tropsch tail gas and swept by the natural gas from the first unit. The hydrogen-containing natural gas is then used as the sweep gas for a second membrane separation unit fed with the hydrogen-depleted shifted Fischer-Tropsch tail gas recovered from the first membrane separation unit. The membrane in the second unit is carbon dioxide selective and a carbon dioxide-containing gas mixture is separated as permeate from the hydrogen-depleted shifted Fischer-Tropsch tail gas and swept by the hydrogen-enriched natural gas from the second unit. The hydrogen- and carbon dioxide-enriched gas mixture may then be fed to the reforming stage. The non-permeate gas mixture recovered from the second unit comprises the one or more inert gases.

In a second embodiment, the shifted Fischer-Tropsch tail gas is fed to a first membrane separation unit fed with a desulphurised natural gas as the sweep gas. The membrane in the first unit is carbon dioxide-selective and a carbon dioxide-containing gas mixture is separated as permeate from the shifted Fischer-Tropsch tail gas and swept by the natural gas from the first unit. The carbon dioxide-depleted shifted Fischer-Tropsch tail gas is then used as the feed gas for a second membrane separation unit. The second membrane separation unit is not swept by natural gas or any other gas on the permeate side. It is nitrogen rejective, i.e. hydrocarbon selective, and a hydrocarbon-containing gas mixture is separated as permeate from the carbon dioxide-depleted shifted Fischer-Tropsch tail gas. If desired to improve the selectivity, the second unit may comprise two identical membrane vessels in series with a compressed recycle around the first nitrogen rejection membrane. The carbon dioxide-enriched natural gas from the first unit and the hydrocarbon-containing gas from the second unit are combined and fed to the reforming stage or fed separately to the reforming stage. The non-permeate gas mixture recovered from the second unit comprises the one or more inert gases.

The effluent from the membrane separation process generally will comprise an inert gas-containing gas stream, which may be used as a fuel, sent for flaring or further separation and purification to recover the components.

In a particularly preferred embodiment, a membrane hydrogen recovery unit is employed and the hydrocarbon feedstock, prior to desulphurisation, is used as the carrier gas on the permeate side of the membrane. In this way, hydrogen is added directly to the hydrocarbon for hydrodesulphurisation purposes. Preferably on the lower pressure side of the membrane, the hydrocarbon feedstock to the GTL plant is used as a 'sweep' gas to mix with the permeating gas, which passes through the membrane. In this way the large flow of sweep gas advantageously ensures that the partial pressure of hydrogen on the lower pressure side remains low even at high hydrogen recovery levels. Another advantage is that this hydrogen recovery can be accomplished without the use of a compressor, which would be required if no sweep gas was being used.

By recovering hydrogen, which would otherwise be going to purge or fuel, the following improvements may be made to the overall hydrocarbon production process.

i) The need for hydrogen to be supplied for hydrodesulphurisation from a separate hydrogen plant could be reduced or eliminated, thus reducing the size of the separate hydrogen plant.

ii) Secondly, if a hydrogen rich permeate stream can be recovered then it allows more natural gas to be processed, with a higher production of Fischer Tropsch products for the same oxygen usage in the reforming section.

The invention is illustrated by reference to the accompanying drawings in which.

Figure 1:
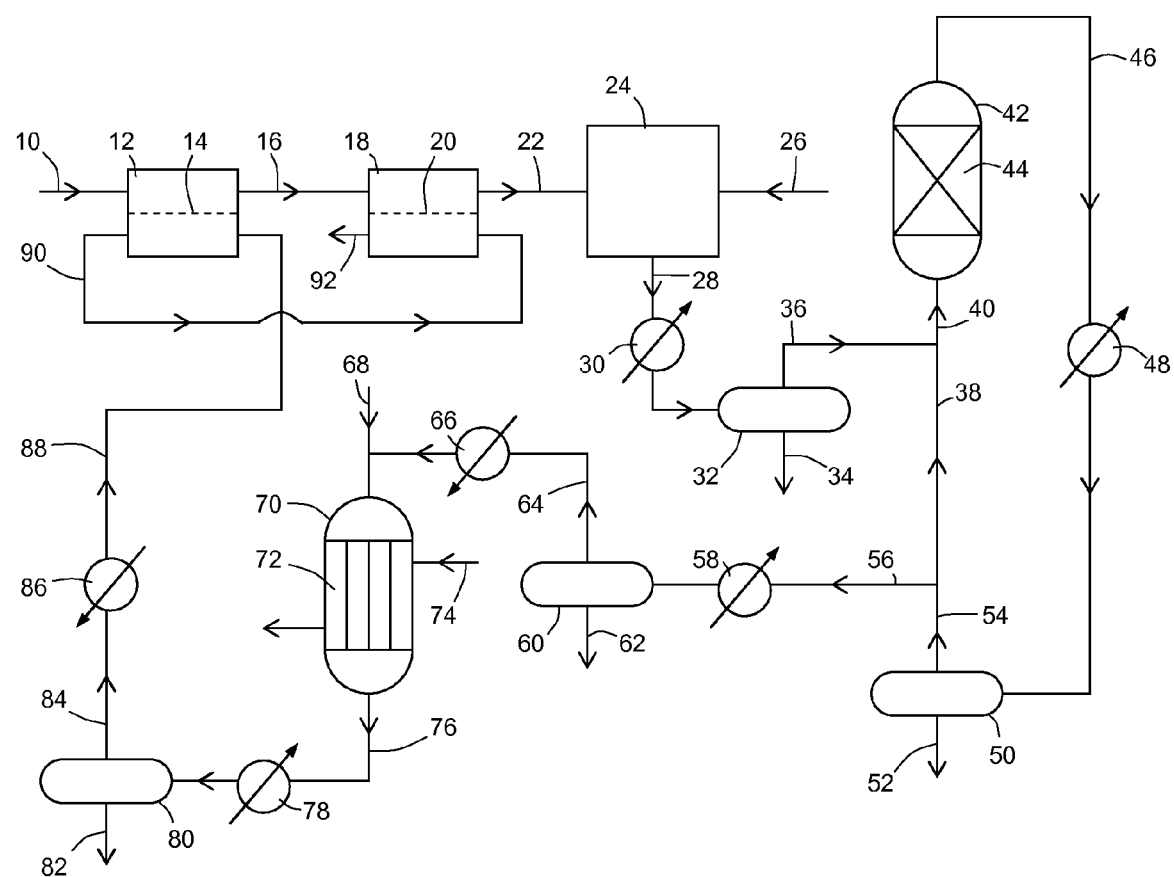
FIG. 1 is a diagrammatic flow-sheet of an embodiment of the invention in which natural gas containing nitrogen is enriched in hydrogen and carbon dioxide derived from a shifted Fischer-Tropsch tail gas.

In FIG. 1, pressurised desulphurised natural gas containing nitrogen is fed via line 10 to a first membrane separation unit 12 containing a hydrogen-selective membrane 14. The natural gas acts as the sweep gas and is enriched in hydrogen permeate as it passes over the membrane 14. The hydrogen-enriched natural gas is fed via line 16 to a second membrane separation unit 18 containing a carbon dioxide-selective membrane 20. The hydrogen-enriched natural gas acts as the sweep gas and is enriched with carbon dioxide permeate as it passes over the membrane 20. The hydrogen- and carbon dioxide-enriched natural gas is fed via line 22 to a synthesis gas generation facility 24 comprising an autothermal reformer or partial oxidation unit fed with oxygen via line 26 supplied by an air separation unit (not shown). In a preferred embodiment, the synthesis gas generation facility 24 comprises a pre-reformer and/or a gas heated reformer and an autothermal reformer, each fed with a portion of the enriched natural gas. The synthesis gas generation unit produces a crude synthesis gas containing nitrogen, steam, hydrogen and carbon oxides with a $H_2$:CO molar ratio of about 2.0:1. The crude synthesis gas is fed via line 28 to a series of heat exchangers 30 in which it is cooled to below the dew point. The cooled synthesis gas is fed to a separator 32 and the process condensate recovered via line 34. The de-watered synthesis gas in line 36 is combined with a FT recycle stream 38 and the combined stream fed via line 40 to one or more Fischer Tropsch reactors 42 containing a bed of Fischer-Tropsch catalyst 44. The Fischer-Tropsch reactions take place in the reactor 42 thereby generating a crude Fischer-Tropsch product stream 46 comprising unreacted gases, liquid and gaseous hydrocarbons and water. A portion of the liquid hydrocarbons may be recovered from the reactor (not shown). The Fischer-Tropsch product stream is cooled in heat exchanger 48 and fed to one or more separators 50 that separate liquid Fischer-Tropsch products via line 52. The gaseous stream 54 recovered from separator 50 is compressed in a compressor (not shown) and divided, and a major portion sent via line 38 as a recycle stream to the Fischer-Tropsch reactor 42. The minor portion, constituting the Fischer-Tropsch tail gas, is recovered from line 54 via line 56. The Fischer-Tropsch tail gas is further compressed in a compressor (not shown) then cooled in heat exchanger 58 to condense any heavy hydrocarbons. The tail gas liquids are separated from the compressed tail gas in separator 60 and recovered as stream 62. The tail gas is fed from the separator 60 via line 64 to a heat exchanger 66 in which it is heated before being mixed with steam fed via line 68. The combined Fischer-Tropsch tail gas/steam mixture is fed to a water gas shift reactor 70 containing a bed of copper/zinc/alumina water-gas shift catalyst 72 in heat exchange with water under pressure fed via line 74. The water gas shift reaction takes place increasing the hydrogen and carbon dioxide content of the Fischer-Tropsch tail gas. In addition, any olefins in the tail gas are hydrogenated to paraffins. The shifted Fischer-Tropsch tail gas is recovered from the shift reactor 70 via line 76 and cooled in heat exchanger 78 to condense the remaining steam. The condensate is separated in separator 80 and recovered as stream 82. The process condensates 82 and 34 may be combined and used in steam generation, e.g. as part of the reforming stage and/or the water-gas shift stage. The de-watered shifted Fischer-Tropsch tail gas is recovered from the separator 80 via line 84, heated in heat exchanger 86 and fed via line 88 to the inlet of the high pressure side of the first membrane separation unit 12. The hydrogen-depleted Fischer-Tropsch tail gas recovered from the first unit 12 is then fed via line 90 to the inlet of the high pressure side of the second membrane separation unit 18. The resulting hydrogen- and carbon dioxide-depleted shifted Fischer-Tropsch tail gas, comprises a high percentage of nitrogen. This inert-gas-containing gas mixture is recovered from the second unit 18 via line 92 and may be used as a fuel, sent for flaring or further separation.

Figure 2:
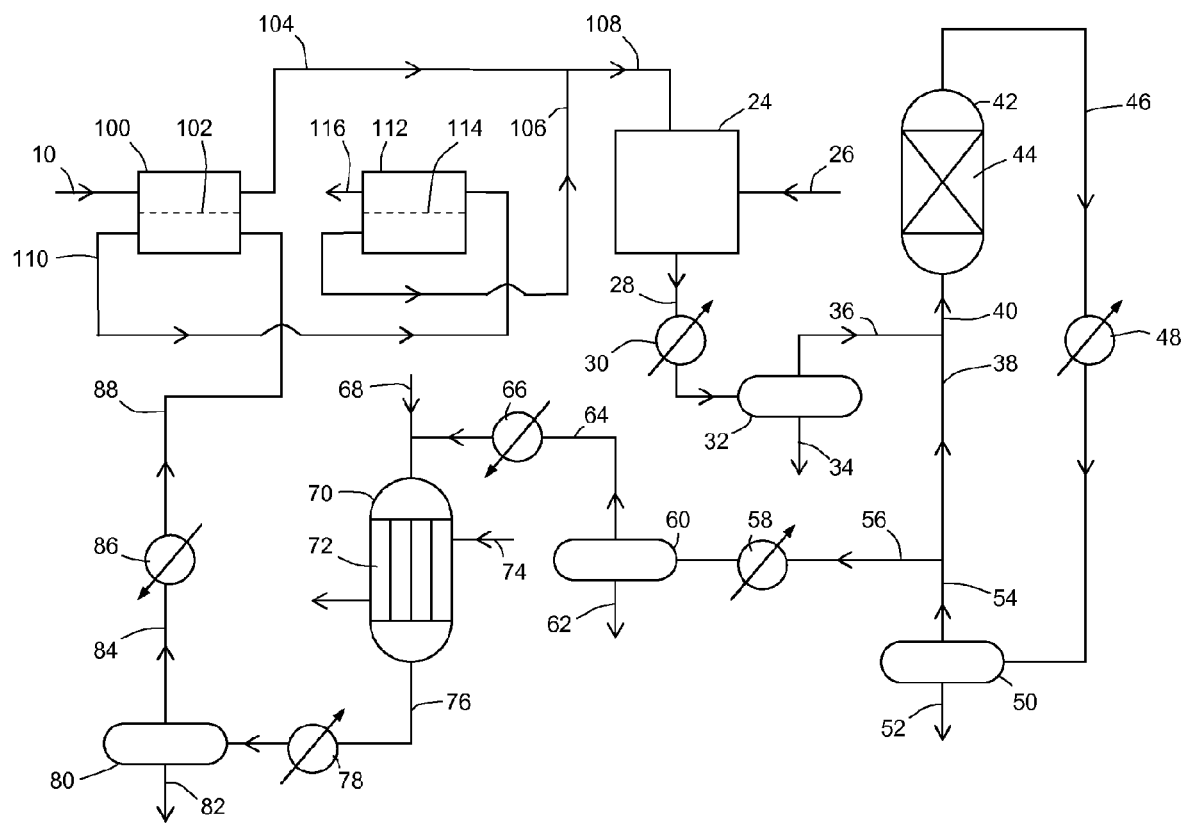
FIG. 2 is a diagrammatic flow-sheet of an embodiment of the invention in which natural gas containing nitrogen is enriched in carbon dioxide and hydrocarbons derived from a shifted Fischer-Tropsch tail gas.

In FIG. 2, the reforming, Fischer-Tropsch and water gas shift stages are the same as those depicted in FIG. 1, but the tail gas treatment is different, resulting in a different reformer feed gas mixture. Thus a pressurised desulphurised natural gas containing nitrogen is fed via line 10 to a first membrane separation unit 100 containing a carbon dioxide-selective membrane 102. The natural gas acts as the sweep gas and is enriched in carbon dioxide permeate as it passes over the membrane 102. The carbon dioxide-enriched natural gas is recovered from the first unit 100 via line 104 and mixed with a hydrocarbon-containing gas in line 106. The mixture of carbon dioxide enriched natural gas and hydrocarbon-containing gas is fed via line 108 to the synthesis gas generation facility 24. The de-watered shifted Fischer-Tropsch tail gas in line 88 is fed to the inlet of the high pressure side of the first membrane separation unit 100. The carbon dioxide-depleted Fischer-Tropsch tail gas recovered from the first unit 100 is then fed via line 110 to the inlet of the high pressure side of a second membrane separation unit 112. This unit contains a nitrogen rejection membrane 114 that allows hydrocarbons to permeate. The hydrocarbon-containing gas permeate is collected from the second unit 112 via line 106 and fed to the carbon dioxide-enriched natural gas stream. The second unit may be configured as two separate vessels in series each containing a nitrogen rejection membrane, with a compressed recycle around the first membrane stage. The carbon dioxide- and hydrocarbon-depleted shifted Fischer-Tropsch tail gas, comprises a high percentage of nitrogen. This inert-gas-containing gas mixture is recovered from the second unit 112 via line 116 and may be used as a fuel, sent for flaring or further separation.

Figure 3:
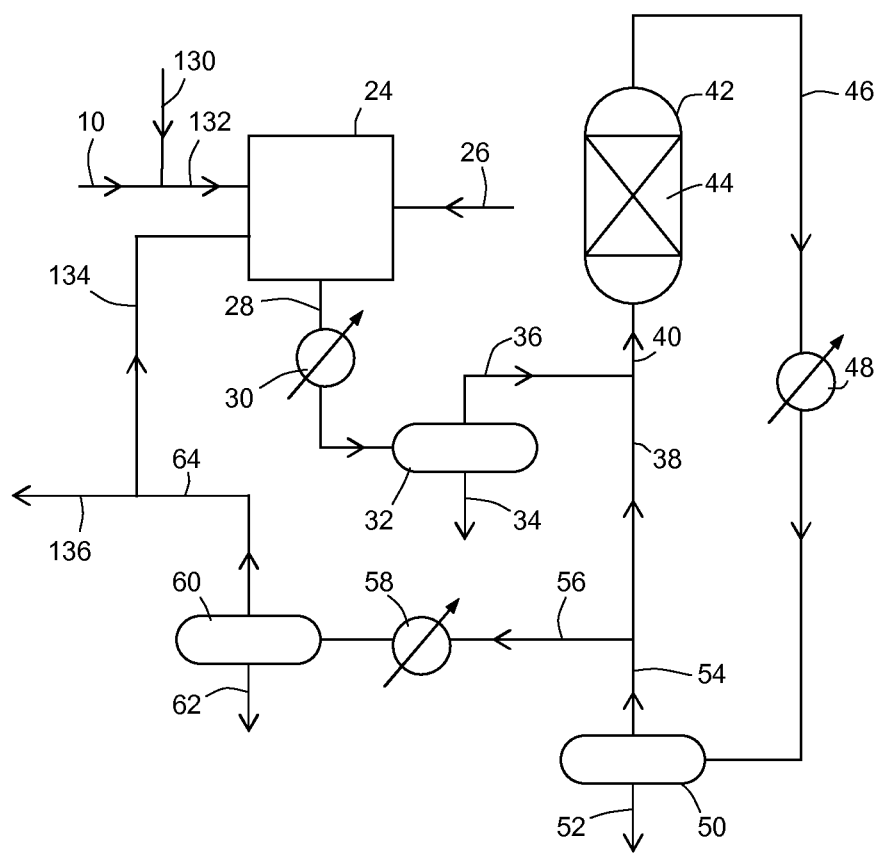
FIG. 3 is a comparative example in which the Fischer-Tropsch tail gas is simply returned to the reforming stage.

In FIG. 3, the reforming and Fischer-Tropsch stages are the same as in FIG. 1 and FIG. 2, but the shift and membrane separation stages are absent. Thus a pressurised desulphurised natural gas containing nitrogen, fed via line 10, is mixed with a hydrogen stream 130 from a hydrogen plant and the resulting natural gas/hydrogen mixture fed via line 132 to the synthesis gas generation facility 24, along with a Fischer-Tropsch tail gas stream 134. The streams 132 and 134 may be combined before feeding to the reforming stage. The Fischer-Tropsch tail gas stream 134 is a portion of the Fischer-Tropsch tail gas stream 64 recovered from the separator 60. Hence, the Fischer-Tropsch tail gas stream 64 recovered from separator 60 is divided; with a minor portion being recovered as a purge stream via line 136 and the other major portion provided to the synthesis gas generation facility 24 via line 134.

The invention is further illustrated by the following calculated examples.

A computer simulation of a flow sheet as depicted in FIG. 3 using a combination of a gas-heated steam reformer and an autothermal reformer to produce the synthesis gas from natural gas at a steam to carbon ration of 0.6 was used as a base case. This had 2% hydrogen added to the natural gas for desulphurisation from a stand-alone hydrogen plant. The application of the water-gas shift and membrane units as depicted in FIGS. 2 and 3 to this scheme was investigated. The consumption of oxygen was kept constant. Steam consumption was kept high enough to the reformers to maintain a key metal dusting parameter constant. Also, the de-watered synthesis gas feed to the Fischer-Tropsch reactor was set to have a $H_2/CO$ ratio of 2:1. Typical commercial membrane performance (as far as relative permeabilities of $H_2$, CO, $CO_2$ and hydrocarbons) was used. These are as follows;

Hydrogen Selective Membrane:

| | |
|---|---|
| $H_2/CO_2$ | 10 |
| $H_2/H_2O$ | 20 |
| $H_2/CO$ | 100 |
| $H_2/N_2$ | 100 |
| $H_2/C_2$ | 200 |
| $H_2/CH_4$ | 100 |
| $H_2/Ar$ | 100 |

Carbon Dioxide Selective Membrane:

| | |
|---|---|
| $CO_2/H_2$ | 5 |
| $CO_2/H_2O$ | 2 |
| $CO_2/N_2$ | 100 |
| $CO_2/CO$ | 100 |
| $CO_2/C_2$ | 100 |
| $CO_2/CH_4$ | 50 |
| $CO_2/Ar$ | 100 |

Hydrocarbon Selective (Nitrogen Rejection) Membrane:

| | |
|---|---|
| $CH_4/N_2$ | 4 |
| $CH_4/Ar$ | 4 |
| $CH_4/CO_2$ | 3.33 |
| $CH_4/H_2O$ | 10 |
| $CH_4/CO$ | 4 |
| $CH_4/C_2$ | 0.25 |
| $CH_4/H_2$ | 2.5 |

EXAMPLE 1

Use of $H_2$— and $CO_2$-Selective Membrane Modules

This case refers to a syngas feed to a Fischer-Tropsch unit with a $H_2/CO$ ratio of 2:1. Shift equilibrium is at 255° C. (isothermal shift at 250° C.); steam to CO ratio of 1.38. While a significant amount of $H_2$ and $CO/CO_2$ is recovered, the fact that there is no hydrocarbon recovery from the tail-gas reduces process carbon efficiency. As a consequence, there is a large carbon/calorific value in the final purge tailgas (TG) due to its hydrocarbon content. Furthermore, in this case, Fischer-Tropsch tail-gas is not fed to the autothermal reformer (as in base case) but to the gas-heated reformer and bypass stream, and contains about 12% $H_2$ and 18% $CO_2$. In addition, the overall steam:carbon ratio in the gas-heated reformer is slightly lower in the membrane case, but there is more $H_2$ and $CO_2$ in the feed. The following table gives comparative results for syngas H2/CO=1.9 case, with extra pure H2 make-up to get to $H_2/CO=2.0$ and the base case.

|  | Comparative Base Case (FIG. 3) | Example 1 (FIG. 1) |
| --- | --- | --- |
| Natural gas feed | 1 | 1.11 |
| FT hydrocarbon make | 1 | 1.02 |
| Steam consumed | 1 | 1.06 |
| Process C efficiency (%) | 92.6* | 85.5 |
| % inerts in FT tail gas ($N_2$) | 27.1 | 8.0 |
| % inerts in FT tail gas (total) | 65.2 | 56.1 |

*Overall carbon efficiency in the base case was about 82.3% allowing for extra fuel needs (extra 11-12% fuel nat gas).

The reduction in $N_2$ content in the hydrocarbon synthesis step increases the final $H_2$ partial pressures by about 25%, which should enable a significant cost saving in the size of some Fischer-Tropsch synthesis equipment. There is also more efficient utilisation of available oxygen (higher gas usage and 2% additional Fischer-Tropsch production from a fixed quantity).

EXAMPLE 2

Use of $CO_2$ Selective Membrane Module and Second Stage $N_2$ Membrane Rejection System This case was looked at for a $H_2/CO$ ratio in the syngas feed of 2.0. Shift equilibrium is at 255° C. (isothermal shift at 250° C.); steam to CO ratio of 0.86. The following table gives comparative results with the base case.

|  | Comparative Base Case (FIG. 3) | Example 2 (FIG. 2) |
| --- | --- | --- |
| Natural gas feed | 1 | 1.07 |
| FT hydrocarbon make | 1 | 0.98 |
| Steam consumed | 1 | 1.07 |
| Process C efficiency (%) | 92.6* | 85.0 |
| % inerts in FT tail gas ($N_2$) | 27.1 | 9.3 |
| % inerts in FT tail gas (total) | 65.2 | 57.1 |

*Overall carbon efficiency in the base case was about 82.3% allowing for extra fuel needs (extra 11-12% fuel nat gas).

This case has a power requirement for compression/recirculation within the $N_2$ rejection membrane system.

This embodiment would be improved by better membrane selectivity performance.

The calculations demonstrate that the use of the combination of water gas shift and membrane separation of the components of the shifted Fischer-Tropsch tail gas can considerably reduce the inert gas content of the hydrocarbon synthesis process.

The invention claimed is:

1. A process for the synthesis of hydrocarbons comprising the steps of:
(i) reforming a hydrocarbon feedstock containing one or more inert gases in one or more reforming stages to generate a synthesis gas comprising the one or more inert gases, steam, hydrogen and carbon monoxide,
(ii) cooling the synthesis gas to below the dew point to condense water and removing the water to give a de-watered synthesis gas,
(iii) synthesising hydrocarbons from said de-watered synthesis gas by the Fischer-Tropsch reaction and separating at least part of the synthesised hydrocarbons, to give a tail gas comprising the one or more inert gases, hydrogen, carbon monoxide and carbon dioxide,
(iv) subjecting a mixture of at least part of the tail gas and steam to the water-gas shift reaction, thereby forming a shifted tail gas having increased hydrogen and carbon dioxide contents,
(v) subjecting the shifted tail gas to one or more stages of membrane separation thereby generating an inert gas-containing gas mixture and one or more of a hydrogen-containing gas mixture, a carbon dioxide-containing gas mixture and a hydrocarbon-containing gas mixture, and
(vi) using one or more of said hydrogen-containing gas mixture, said carbon dioxide-containing gas mixture and said hydrocarbon-containing gas mixture in a reformer feed stream, wherein the hydrocarbon feedstock is used as a component of the sweep gas on the permeate side of at least one of the membrane separation stages.

2. The process according to claim 1 wherein the reforming step includes a step of steam reforming.

3. The process according to claim 1 wherein the reforming step includes a step of partial oxidation.

4. The process according to claim 1 wherein the reforming step includes a step of autothermal reforming.

5. The process according to claim 2 wherein the reforming step also includes a step of pre-reforming.

6. The process according to claim 1 wherein said hydrocarbon feedstock is divided and fed to more than one reforming step.

7. The process according to claim 1 wherein one or more of said hydrogen-containing gas mixture, said carbon dioxide-containing gas mixture and said hydrocarbon-containing gas mixture is fed to a pre-reformer, a steam reformer, a secondary reformer or an autothermal reformer.

8. The process according to claim 1 wherein the reforming step comprises primary steam reforming in a steam reformer and secondary reforming in a secondary reformer and one or more of said hydrogen-containing gas mixture, said carbon dioxide-containing gas mixture and said hydrocarbon-containing gas mixture is fed to the primary reformed gas before it is fed to the secondary reformer.

9. The process according to claim 1 wherein the hydrocarbon feedstock is a natural gas, including associated gas.

10. The process according to claim 1 wherein, the shifted Fischer-Tropsch tail gas is fed to a first membrane separation unit fed with a desulphurized natural gas as the sweep gas, said unit containing a hydrogen-selective membrane that produces a hydrogen-containing gas mixture permeate that is swept by the natural gas from the first unit to a second membrane separation unit fed with a hydrogen-depleted shifted Fischer-Tropsch tail gas recovered from the first membrane separation unit, said second unit containing a carbon dioxide-selective membrane that produces a carbon dioxide-containing gas mixture permeate from the hydrogen-depleted shifted Fischer-Tropsch tail gas that is swept from the second unit by the hydrogen-enriched natural gas to form a reformer feed gas mixture.

11. The process according to claim 1 wherein the shifted Fischer-Tropsch tail gas is fed to a first membrane separation unit fed with a desulphurized natural gas as the sweep gas, said unit containing a carbon dioxide-selective membrane that produces a carbon dioxide-containing gas mixture permeate that is swept by the natural gas from the first unit, and wherein the carbon dioxide-depleted shifted Fischer-Tropsch tail gas is then used as a feed gas for a second membrane separation unit containing a hydrocarbon selective membrane that produces a hydrocarbon-containing gas mixture permeate and wherein the carbon dioxide-enriched natural gas from the first unit and the hydrocarbon-containing gas from the second unit are combined and fed to the reforming stage, or fed separately to the reforming stage.

12. The process according to claim 3 wherein the reforming step also includes a step of pre-reforming.

13. The process according to claim 4 wherein the reforming step also includes a step of pre-reforming.

* * * * *